United States Patent [19]

Coy et al.

[11] 4,127,528

[45] Nov. 28, 1978

[54] NOVEL DERIVATIVES OF ALPHA-ENDORPHIN, INTERMEDIATES THEREFOR AND COMPOSITIONS AND METHODS EMPLOYING SAID DERIVATIVES

[76] Inventors: David H. Coy, 4319 Perrier St., New Orleans, La. 70115; Abba J. Kastin, 4400 Morales St., Metairie, La. 70002

[21] Appl. No.: 807,140

[22] Filed: Jun. 16, 1977

[51] Int. Cl.$^2$ .................... C08L 37/00; C07C 103/52; A61K 37/00

[52] U.S. Cl. .................................. 260/8; 260/112.5 R; 424/177

[58] Field of Search .................. 260/112.5 R, 112.5 E, 260/8; 424/177

[56] References Cited

U.S. PATENT DOCUMENTS 4,038,222  7/1977  Li ......................................... 424/177

OTHER PUBLICATIONS

Cox, et al., Proc. Natl. Acad. Sci. USA 73, 1976, pp. 1821-1823.
Lazarus, et al., Proc. Natl. Acad. Sci. USA 73, 1976, pp. 2156-2159.
Ling, et al., Chem. Abst. 86, 1977, pp. 38887h.
Ling, et al., Proc. Natl. Acad. Sci. USA 73, 1976, pp. 3308-3310.
Guillemin, et al., Biochimie 1976, pp. 783-785.
Bradbury, et al., Nature 260, 1976, pp. 793-795.
Li, et al., Proc. Natl. Acad Sci. USA 73, 1976, pp. 1145-1148.

Coy, et al., Biochem. and Biophys. Res. Comm. 73, 1976, pp. 632-638.
Pert, et al., Opiates and Endogenous Opioid Peptides 1976, pp. 79-86.
Plotnikoff, et al., Life Science 19, pp. 1283-1288, 1976.
Kosterlitz, et al., Life Science 17, pp. 91-96, 1975.
Pert, et al. Science, 194, 330-332, 1976.
Ling, et al., Biochem. and Biophys. Res. Comm. 74, 1977, pp. 248-255.
Marks, et al., Biochem. and Biophys. Res. Comm. 74, 1977, pp. 1552-1559.

*Primary Examiner*—Delbert R. Phillips
*Attorney, Agent, or Firm*—Joyce R. Niblack

[57] ABSTRACT

Novel hexadecapeptides represented by formula I

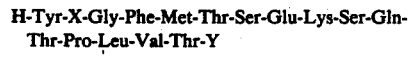

H-Tyr-X-Gly-Phe-Met-Thr-Ser-Glu-Lys-Ser-Gln-Thr-Pro-Leu-Val-Thr-Y wherein X is a chiral residue of a D-amino acid selected from the group consisting of D-alanine, D-leucine, D-isoleucine, D-valine, D-phenylalanine, D-tyrosine, D-tryptophan, D-serine, D-threonine, D-methionine, D-glutamic acid, D-glutamine, D-aspartic acid, D-asparagine, D-aroline, D-histidine, D-lysine and D-arginine; Y is selected from the group consisting of hydroxy, amino, loweralkylamino, dialkylamino and lower alkoxy; and the pharmaceutically acceptable salts thereof; intermediates useful in making the novel compounds; and pharmaceutical compositions and methods employing the novel compounds.

20 Claims, No Drawings

NOVEL DERIVATIVES OF ALPHA-ENDORPHIN, INTERMEDIATES THEREFOR AND COMPOSITIONS AND METHODS EMPLOYING SAID DERIVATIVES

BACKGROUND OF THE INVENTION

While there are a number of analgesic agents currently utilized to relieve mild to severe pain, the search for improved analgesics is a continuing one because of the numerous problems associated with the presently available agents. Aspirin and related salicylates are considered to be non-narcotic analgesic agents useful for relieving mild to moderate pain in addition to their usefulness as anti-inflammatory and anti-pyretic agents. However, the ingestion of salicylic acid or related salicylates may result in epigastric distress, nausea and vomiting. This widely used class of non-narcotic analgesic agents may also cause gastric ulceration and even hemorrhage both in experimental animals and man. Exacerbation of peptic ulcer symptoms and erosive gastritis have all been reported in patients on high dose therapy, i.e., arthritis patients. Aspirin is also one of the most common causes of drug poisoning in young children and has a potential of serious toxicity if used improperly.

Acetaminophen is also considered to be a non-narcotic analgesic agent useful in treating mild pain associated with simple headache, common muscular aches, etc. While acetaminophen is particularly useful for patients who cannot take aspirin, e.g., ulcer patients, its use is contraindicated in individuals who have exhibited a sensitivity to it. In addition to their drawbacks in view of their potential side effects, the mild non-narcotic analgesic agents are not sufficiently potent to relieve the severe pain associated with surgery, cancer and the like. Unfortunately, the potent analgesic agents capable of relieving such severe pain are also narcotic agents and their use entails the risk of producing physical dependence. There are as yet no agents effective against severe pain that are entirely free of this risk.

Thus, there is an urgent need for improved analgesic agents for treating mild as well as severe pain. The present invention provides such agents.

In addition to the need for improved analgesic agents, there is also a need for improved psychotropic agents to provide an alternative to current therapy. The compounds of this invention, in addition to their analgesic activity, also exhibit anti-depressant, tranquilizing, sedative and hypnotic activity. Thus, their usefulness as analgesic agents is enhanced, since many patients suffering from pain also exhibit varying states of anxiety and depression.

A recently identified pentapeptide, methionine enkephalin, has the following structure H-Tyr-Gly-Gly-Phe-Met-OH [see Hughes et al., *Nature*, 258, 577 (1975)]. This peptide is found in many areas of the brain where it appears to act as a neurotransmitter or neuromodulator in a central pain suppressive system. The natural peptide binds stereo-specifically to partially purified brain opiate receptor sites [for instance, see Bradbury et al., *Nature*, 260, 793 (1976)], is very active in bioassays for opiate activity, but exhibits only weak analgesic activity of short duration when injected directly into the brain of the rat [for instance, see Belluzzi et al., *Nature*, 260, 625 (1976)].

In addition, several C-terminal fragments of a 91 chain length peptide known as human, porcine or camel β-lipotropin having the pentapeptide sequence of methionine enkephalin at their N-terminus have been isolated from the pituitary and found to exhibit potent in vitro opioid activity in binding to partially purified brain opiate receptor sites. [see Ling and Guillemin, *Proc. Natl. Acad. Sci. USA* 73, 3308 (1976) and *Proc. Natl. Acad. Sci. USA* 73, 1821 (1976)]. The reported fragments have been characterized as α-endorphin (61–76), β-endorphin (61–91), γ-endorphin (61–77) and δ-endorphin (61–87), and β-lipotropin fragments (61–64 61–68, 61–69, 61–79 and 70–79. Unlike the enkaphalins, the endorphins possesses some pharmacological activity when administered intracerebrally or parenterally. The present invention is directed to novel derivatives of mammalian α-endorphin which are highly active by a variety of routes of administration and thus are useful as pharmacological and veterinary agents.

We have unexpectedly found that the incorporation of a D-amino acid, such as D-alanine, for the penultimate glycine residue at the N terminus of a α-endorphin greatly enhances the analgesic activity of these compounds. In addition to their analgesic activity, the compounds also exhibit excellent anti-depressant, sedative, hypnotic, and tranquilizing activity, and additionally have veterinary utility as growth hormone releasing agents and prolactin releasing agents.

SUMMARY OF THE INVENTION

This invention relates to novel hexadecapeptides, and more specifically relates to novel α-endorphin derivatives of mammalian β-lipotropin fragment 61–76 which are useful as analgesic, tranquilizer, sedative, hypnotic, anti-depressant agents growth hormone releasing agents and prolactin releasing to intermediates useful in the preparation of the novel hexadecapeptides, and to pharmaceutical compositions and methods employing such novel hexadecapeptides, and to pharmaceutical compositions and methods employing such novel hexadecapeptides.

DETAILED DESCRIPTION OF PREFERRED EMBODIMENTS

The compounds of this invention are hexadecapeptides represented by formula I and having the following amino acid sequence:

H-Tyr-X-Gly-Phe-Met-Thr-Ser-Glu-Lys-Ser-Gln-Thr-Pro-Leu-Val-Thr-Y  (I)

wherein
X is a chiral residue of a D-amino acid selected from the group consisting of D-alanine, D-leucine, D-isoleucine, D-valine, D-phenylalanine, D-tyrosine, D-tryptophan, D-serine, D-threonine, D-methionine, D-glutamic acid, D-glutamine, D-aspartic acid, D-asparagine, D-lysine D-proline, D-histidine and D-arginine; Y is selected from the group consisting of hydroxy, amino, aminoloweralkyl, aminodiloweralkyl, and lower alkoxy; and the pharmaceutically acceptable salts thereof.

All chiral amino acid residues identified herein are in the natural or L-configuration unless otherwise specified.

In keeping with standard peptide nomenclature, abbreviations for chiral amino acid residues have been used herein as follows:

| | | | |
|---|---|---|---|
| Tyr | - L-tyrosine | Ile | - L-isoleucine |
| D-Tyr | - D-tyrosine | D-Ile | - D-isoleucine |
| Gly | - glycine | Leu | - L-leucine |
| Phe | - L-phenylalanine | D-Leu | - D-leucine |
| D-Phe | - D-phenylalanine | Thr | - L-threonine |
| Met | - L-methionine | D-Thr | - D-threonine |
| D-Met | - D-methionine | Val | - L-valine |
| Ala | - L-alanine | D-Val | - D-valine |
| D-Ala | - D-alanine | Pro | - L-proline |
| Ser | - L-serine | D-Pro | - D-proline |
| D-Ser | - D-serine | Gln | - L-glutamine |
| Lys | - L-lysine | D-Gln | - D-glutamine |
| D-Lys | - D-lysine | Glu | - L-glutamic acid |
| Asn | - L-asparagine | D-Glu | - D-glutamic acid |
| D-Asn | - D-asparagine | Trp | - L-tryptophan |
| His | - L-histidine | D-Trp | - D-tryptophan |
| D-His | - D-histidine | D-Asp | - D-aspartic acid |

The term "pharmaceutically acceptable salts," as used herein, refers to the non-toxic alkali metal, alkaline earth metal and ammonium salts commonly used in the pharmaceutical industry including the sodium, potassium, lithium, calcium, magnesium, barium and ammonium salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The term "lower alkyl" refers to straight and branched chain alkyl groups having from 1 to 6 carbon atoms.

The term "lower alkoxy" refers to straight and branched chain alkoxy groups having from 1 to 6 carbon atoms such as methoxy, ethoxy, and the like.

Also contemplated within the scope of the present invention are the following intermediates which are useful in preparing the hexadecpeptides of this invention and are represented by Formula II:

$R_1$-Tyr($R_2$)-X'-Gly-Phe-Met-Thr($R_3$)-Ser($R_3$)-Glu($R_4$)-Lys($R_5$)-Ser($R_3$)-Gln-Thr($R_3$)-Pro-Leu-Val-Thr($R_3$)-Y  (II)

wherein

X' is equal to X as defined in Formula I above, except in the case of D-threonine, D-serine, D-tyrosine, D-glutamic acid, D-arginine, D-asparagine and D-lysine, in which cases X is a chiral residue of a D-amino acid as defined in Formula I protected by an $R_2$, $R_3$, $R_4$ or $R_5$ protecting group as defined below:

$R_1$ is a solid state peptide synthesis N-terminus protecting group selected from the group consisting of acyl type protecting groups, aromatic urethan-type protecting groups, alkyl type protecting groups, trialkylsilane groups, and aliphatic urethan protecting groups;

$R_2$ is a protecting group for the phenolic hydroxyl group of tyrosine selected from the group consisting of tetrahydropyranyl, tert-butyl, trityl, benzyl, 2,4-dichlorobenzyl, benzyloxycarbonyl or 2-bromobenzyloxycarbonyl (2-Br-Z);

$R_3$ is a protecting group for the alcohol hydroxy functions of serine and threonine, and is selected from the group defined hereinbefore for $R_2$;

$R_4$ is a protecting group for the gamma carboxyl group of glutamic acid selected from the group consisting of tert-butyl, benzyl, or 4-chlorobenzyl.

$R_5$ is a protecting group for the epsilon amino group of lysine selected from the group consisting of trifluoroacetyl, benzyloxycarbonyl or, preferably, 2-chlorobenzyloxycarbonyl; and $R_6$ is a protecting group for the guanidine group of arginine and is either nitro or tosyl.

Y is as defined in Formula I above or a derivatized insoluble polystyrene resin support represented by Formula III or IV:

  (III)

  (IV)

The term "acyl type protecting groups" refers to groups illustrated by but not restricted to formyl, trifluoroacetyl, tosyl, nitrosulfonyl, and the like.

The term "aromatic urethan-type protecting groups" is represented by groups such as benzyloxycarbonyl, p-methoxybenzyloxycarbonyl, p-biphenylisopropyloxycarbonyl, and the like.

The term "cycloalkyl urethan protecting group," as used herein, refers to groups such as cyclopentyloxycarbonyl, adamantyloxycarbonyl, cyclohexyloxycarbonyl, isobornyloxycarbonyl, etc.

"Alkyl type protecting groups" are those commonly used in the art such as the trityl group.

"Trialkylsilane groups" include compounds such as trimethylsilane, triethylsilane, tributylsilane, and the like.

The preferred protecting groups, the "aliphatic urethan protecting groups," include tert-butyloxycarbonyl, diisopropyloxycarbonyl, isopropyloxycarbonyl, allyloxycarbonyl, and the like.

The polystyrene resin support is preferably a copolymer of styrene with 1–2 weight percent of divinyl benzene as a cross-linking agent which causes the polystyrene polymer to be completely insoluble in most organic solvents. In Formula IV, $\phi$ is phenyl.

In selecting a particular side-chain protecting group to be used in the synthesis of the peptides, several conditions must be met: (a) the protecting group must be stable to the reagent and under reaction conditions selected for removing the α-amino protecting group at each step of the synthesis; (b) the protecting group must retain its protecting properties and not be chemically modified; and (c) the side-chain protecting group must be removable at the end of the solid-phase synthesis under reaction conditions that will not alter the peptide chain.

The peptides are prepared using standard solid-phase techniques. The synthesis is commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif. and the preparation of the hydroxymethyl resin is described by Bodonszky et al., *Chem. Ind.* (London) 38, 1597 (1966).

The benzhydrylamine resin has been described by Pietta and Marshall, *Chem. Commun.*, 650 (1970) and is commercially available from Beckman Instruments, Palo Alto, Calif.

In the preparation of the compounds of this invention, an α-amino protected amino acid is coupled to the chloromethylated resin with the aid of, for example, cesium bicarbonate catalyst, according to the method described by Gisin, *Helv. Chim. Acta*, 56, 1476 (1973). After the initial coupling, the α-amino protecting group is removed by a choice of reagents including trifluoroacetic acid or hydrochloric acid solutions in organic solvents at room temperature. After removal of the α-amino protecting group, the remaining protected amino acids are coupled stepwise in the desired order to obtain the compounds of Formula II. Each protected amino acid is generally reacted in a 3-fold excess using an appropriate carboxyl group activator such as dicyclohexylcarbodiimide in solution in, for example, methylene chloride-dimethylformamide mixtures.

After the desired amino acid sequence has been completed, the desired peptide is removed from the resin support by treatment with a reagent such as hydrogen fluoride which not only cleaves the peptide from the resin, but also cleaves all remaining side-chain protecting groups. When the chloromethylated resin is used, hydrogen fluoride treatment results in the formation of the free peptide acids of Formula I (Y=OH). When the benzhydrylamine resin is used, hydrogen fluoride treatment results directly in the free peptide amides of Formula I (Y=NH$_2$). Alternatively, when the chloromethylated resin is employed, the side-chain protected peptide can be cleaved by treatment of the peptide-resin with ammonia to give the desired side-chain protected amide or with an alkylamine to give a side-chain protected alkylamide. Side-chain protection is then removed in the usual fashion by treatment with hydrogen fluoride to give the free amides or alkylamides.

In preparing the esters of this invention (Y=lower alkoxy), the resin used to prepare the acids of Formula I (Y=OH) is employed and the side-chain protected group is cleaved with base and the appropriate alcohol, i.e., methanol. Side-chain protection is then removed in the usual fashion by treatment with hydrogen fluoride to obtain the desired ester.

The solid-phase procedure discussed above is well known in the art and has been essentially described by J. M. Stewart, *Solid Phase Peptide Synthesis (Freeman and Co., San Francisco, 1969)*.

The compounds of Formula I are useful as analgesics, anti-depressants, tranquilizers, sedatives or hypnotics when administered to mammalian hosts at dosages of from 0.001 to 100 mg/kg of body weight daily, preferably in divided dosages. The compounds are preferably administered by parenteral routes, i.e., the intravenous, intraperitoneal, intramuscular or subcutaneous routes of administration, but may also be administered by a variety of other routes including the oral or sublingual, or by vaginal, rectal or nasal routes of administration. Accordingly, one aspect of the present invention includes pharmaceutical compositions suitable for such routes of administration.

The analgesic activity of the compounds of Formula I was established in the rat tail flick test as described by D'Amour and Smith, *J. Pharmac. Exp. Ther.*, 72, 74 (1941). The presently preferred analgesic agent of this invention is D-Ala$^2$-β-lipotropin fragment (61–76) (also known as D-Ala$^2$-α-endorphin.

The anti-depressant (stimulant) activity and the tranquilizing and sedative-hypnotic activity of the compounds of Formula I were first established in the open field test described by Kulkarni et al. *Pharmakopsychiatrie Neuro-Psychopharamkologie* 8(1): pp. 45–50 (1975) and the self stimulation test described by Bailey et al., *Research Communications in Chemical Pathology and Pharmacology* 11(4): pp. 543–552 (1975).

The dosage administered depends upon the desired effect. For example, the degree of analgesia produced by the compounds of this invention may be varied by varying the dosage. Anti-depressant activity is observed at the lower dosages, i.e., 0.001 to 5 mg./kg., and sedation or tranquilization is produced by dosages of greater than 5 ml./kg. of body weight.

The following compounds are illustrative of the hexadecapeptides of Formula I. Compounds of Formula I will hereinafter be designated as derivatives of α-endorphin. The D-amino acid is designated as being in the 2-position. Compounds wherein Y— is OH are named as substituted α-endorphins and are illustrated by the following:

D-Ala$^2$-α-endorphin;
D-Leu$^2$-α-endorphin;
D-Ile$^2$-α-endorphin;
D-Val$^2$-α-endorphin;
D-Phe$^2$-α-endorphin;
D-Tyr$^2$-α-endorphin;
D-Trp$^2$-α-endorphin;
D-Ser$^2$-α-endorphin, sodium salt;
D-Thr$^2$-α-endorphin;
D-Met$^2$-α-endorphin; calcium salt;
D-Glu$^2$-α-endorphin;
D-Gln-$^2$-α-endorphin; ammonium salt;
D-Asp$^2$-α-endorphin;
D-Asn$^2$-α-endorphin;
D-Lys$^2$-α-endorphin;
D-Arg$^2$-α-endorphin;

The endorphin amides of this invention include but are not limited to the following:
D-Ala$^2$-α-endorphin amide;
D-Leu$^2$-α-endorphin amide;
D-Ile$^2$-α-endorphin amide;
D-Val$^2$-α-endorphin amide;
D-Phe$^2$-α-endorphin amide;
D-Tyr$^2$-α-endorphin amide;
D-Trp$^2$-α-endorphin amide;
D-Ser$^2$-α-endorphin amide;
D-Thr$^2$-α-endorphin amide;
D-Met$^2$-α-endorphin amide;
D-Glu$^2$-α-endorphin amide;
D-Gln$^2$-α-endorphin amide;
D-Asp$^2$-α-endorphin amide;
D-Asn$^2$-α-endorphin amide;
D-Lys$^2$-α-endorphin amide;
D-Arg$^2$-α-endorphin amide;
D-Ala$^2$-α-endorphin amide hydrochloride;
D-Leu$^2$-α-endorphin amide citrate;
D-Ile$^2$-α-endorphin amide hydrobromide;
D-Val$^2$-α-endorphin amide hydroiodide;
D-Phe$^2$-α-endorphin amide hydrochloride;
D-Tyr$^2$-α-endorphin amide sulfate;
D-Trp$^2$-α-endorphin amide lactate;
D-Ser$^2$-α-endorphin amide mapsylate;
D-His$^2$-α-endorphin amide;
D-Thr$^2$-α-endorphin amide oleate;
D-Met$^2$-α-endorphin amide valerate;

D-Glu$^2$-α-endorphin amide tosylate;
D-Gln$^2$-α-endorphin amide disulfate;
D-Asp$^2$-α-endorphin amide benzoate;
D-Asn$^2$-α-endorphin amide acetate;
D-Lys$^2$-α-endorphin amide laurate;
D-Arg$^2$-α-endorphin amide phosphate;
D-Ala$^2$-α-endorphin methylamide;
D-Leu$^2$-α-endorphin ethylamide;
D-Ile$^2$-α-endorphin propylamide;
D-Val$^2$-α-endorphin n-butylamide;
D-Phe$^2$-α-endorphin tert-butylamide;
D-Tyr$^2$-α-endorphin sec-butylamide;
D-Trp$^2$-α-endorphin n-pentylamide;
D-Ser$^2$-α-endorphin ethylamide;
D-Thr$^2$-α-endorphin dimethylamide;
D-Met$^2$-α-endorphin diethylamide;
D-Glu$^2$-α-endorphin n-propylamide;
D-Gln$^2$-α-endorphin-iso-propylamide; and the like.

Esters of this invention include but are not limited to the following:

D-Ala$^2$-α-endorphin, methyl ester;
D-Val$^2$-α-endorphin, ethyl ester;
D-Met$^2$-α-endorphin, n-propyl ester;
D-Phe$^2$-α-endorphin, iso-propyl ester;
D-Glu$^2$-α-endorphin, n-butyl ester;
D-Gln$^2$-α-endorphin, n-pentyl ester;
D-Ser$^2$-α-endorphin, n-hexyl ester; and the like.

The following examples further illustrate the present invention:

EXAMPLE 1

Preparation of 0-2-Bromobenzyloxycarbonyl-L-tyrosyl-D-alanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH$_2$-resin.

Tert-butyloxycarbonyl-O-benzyl-threonine-O—CH$_2$-resin (1.0 mmole), prepared by the method of Gisin, *Helv. Chim. Acta*, 56, 1476 (1973) was placed in the reaction vessel of a Beckman Model 990 automatic peptide synthesizer, programmed to carry out the following cycle of washes and reactions: (a) methylene chloride; (b) 25% trifluoroacetic acid in methylene chloride (2 times for 1.5 and 15 minutes each); (c) 50% trifluoroacetic acid in methylene chloride (15 minutes); (d) methylene chloride; (e) ethanol; (f) methylene chloride; (g) 10% triethylamine in methylene chloride (2 times for 5 minutes each); and (h) methylene chloride.

The deprotected resin was then stirred with tert-butyloxycarbonyl (t-Boc) valine (3.0 mmoles) in methylene chloride, and dicyclohexylcarbodiimide (3.0 mmoles) was added thereto. The mixture was stirred at room temperature for 2 hours and the peptide resin was then washed successively with methylene chloride, ethanol and methylene chloride. Two percent N-acetylimidazole in methylene chloride was then added and the mixture stirred for 15 minutes in order to irreversibly acetylate unreacted free amino groups. The resin was then washed with methylene chloride followed by ethanol and then steps (a) through (h) were repeated as described above.

The remaining 14 t-Boc-amino acids are then coupled successively by the same cycle of washes and reactions and the completed peptide resin was washed with methanol (3 times) and dried under reduced pressure whereupon 5.22g of the desired resin was obtained.

EXAMPLE 2

Preparation of L-tyrosyl-D-alanyl-glycyl-L-phenylalanyl-L-methionyl-L-threonyl-L-seryl-L-glutamyl-L-lysyl-L-seryl-L-glutaminyl-L-threonyl-L-prolyl-L-leucyl-L-valyl-L-threonine. (D-Ala$^2$-α-endorphin).

D-Ala$^2$-α-endorphin was prepared by treating 0.5 mmole of the peptide resin of Example 1 with hydrogen fluoride (40 ml) and anisole (4 ml) at 0° for 45 minutes. The hydrogen fluoride was removed under reduced pressure and the anisole removed by washing with ethyl acetate.

The crude peptide was purified by gel filtration on a column (2.5 × 95 cm) of Sephadex G50 gel by elution with 2 molar acetic acid and fractions shown to contain a major peak by uv absorption at 280 nm were pooled and evaporated to dryness. The residual oil is applied to a column (2.5 × 95 cm) of Sephadex G50 previously equilibrated with the lower phase followed by the upper phase of 0.1% acetic acid: n-butanol: pyridine (11:5:3) solvent system. Elution with the upper phase yielded a major symmetrical peak, determined by Folin-Lowry measurements, and material from this area was evaporated to dryness and lyophilized repeatedly from water to yield 328 mg of a white powder.

The product was homogeneous by thin layer chromatography in 4 solvent systems on silica gel plates when loads of 30 μg were applied and visualized by exposure to ninhydrin reagent followed by chlorine/starch-potassium iodide reagent. The following R$_f$ values were obtained:

(A) n-Butanol:acetic acid:water (4:1:5 upper phase) 0.15; (B) ethyl acetate:pyridine:acetic acid:water (5:5:1:3), 0.69; (C) (iso-propanol:1M acetic acid (2:1), 0.63; (D) n-butanol:acetic acid:water:ethyl acetate (1:1:1:1), 0.54.

EXAMPLE 3

0-2-Bromobenzyloxycarbonyl-L-tyrosyl-D-leucyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl—O—CH$_2$ resin is prepared by the method of Example 1, using t-Boc-D-leucine, instead of the t-Boc-D-alanine.

EXAMPLE 4

D-Leu$^2$-α-endorphin is prepared by the method of Example 2, from the peptide resin of Example 3.

EXAMPLE 5

0-2-Bromobenzyloxycarbonyl-L-tyrosyl-D-isoleucylglycyl-L-phenylalanyl-L-methionyl-O-benzyl-L-threonyl-O-benzyl-L-seryl-gamma-benzyl-L-glutamyl-N-epsilon-2-chlorobenzyloxycarbonal-L-lysyl-O-benzyl-L-seryl-L-glutaminyl-O-benzyl-L-threonyl-L-prolyl-L-leucyl-L-leucyl-L-valyl-O-benzyl-L-threonyl-O-CH$_2$-resin is prepared by the method of Example 1, using the corresponding t-Boc-D-isoleucine instead of the t-Boc-D-alanine.

EXAMPLE 6

D-Ile²-α-endorphin is prepared by the method of Example 2, from the peptide resin of Example 5.

EXAMPLE 7

0-2-Bromobenzyloxycarbonyl-L-tyrosyl-D-valyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-servl-L-glutaminyl-O-benzyl-L-threonyl-L-prolyl-L-valyl-O-benzyl-L-threonyl-O-CH₂ -resin is prepared by the method of Example 1, using the corresponding t-Boc-D-valine instead of the t-Boc-D-alanine.

EXAMPLE 8

D-Val²-α-endorphin is prepared by the method of Example 2, from the peptide resin of Example 7.

EXAMPLE 9

0-2-Bromobenzyloxycarbonyl-L-tyrosyl-D-phenylalanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH₂ resin is prepared by the method of Example 1, using the corresponding t-Boc-D-phenylalanine instead of the t-Boc-D-alanine.

EXAMPLE 10

D-Phe²-α-endorphin is prepared by the method of Example 2 from the peptide resin of Example 9.

EXAMPLE 11

0-2-Bromobenzyloxycarbonyl-L-tyrosyl-2-bromobenzyloxycarbonyl-D-tyrosyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH₂-resin is prepared by the method of Example 1, using the corresponding t-Boc-D-tyrosine derivative instead of t-Boc-D-alanine.

EXAMPLE 12

D-Tyr²-α-endorphin is prepared by the method of Example 2 from the peptide resin of Example 11.

EXAMPLE 13

0-2-Bromobenzyloxycarbonyl-L-tyrosyl-D-tryptophanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH₂-resin is prepared by the method of Example 1, using t-Boc-D-tryptophan instead of the t-Boc-D-alanine.

EXAMPLE 14

D-Trp²-α-endorphin is prepared by the method of Example 2 from the peptide resin of Example 13.

EXAMPLE 15

0-2-Bromobenzyloxycarbonyl-L-tyrosyl-O-benzyl-D-seryl-glycyl-L-phenylalanyl-L-methionyl-O-benzyl-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-proplyl-L-leucyl-L-valyl-O-benzyl-L-threonyl-O-CH₂-resin is prepared by the method of Example 1, using the corresponding t-Boc-serine derivative instead of the t-Boc-D-alanine derivative.

EXAMPLE 16

D-Ser²-α-endorphin is prepared by the method of Example 2 from the peptide resin of Example 15.

EXAMPLE 17

0-2-Bromobenzyloxycarbonyl-L-tyrosyl-O-benzyl-D-threonyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH₂-resin is prepared by the method of Example 1, using the corresponding t-Boc-D-threonine derivative.

EXAMPLE 18

D-Thr-hu 2-α-endorphin is prepared by the method of Example 2 from the peptide resin of Example 17.

EXAMPLE 19

0-2-Bromobenzyloxycarbonyl-L-tyrosyl-D-methionyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH₂-resin is prepared by the method of Example 1, using the corresponding t-Boc-D-methionine instead of t-Boc-D-alanine.

EXAMPLE 20

D-Met²-α-endorphin is prepared by the method of Example 2 from the peptide resin of Example 19.

EXAMPLE 21

0-2-Bromobenzyloxycarbonyl-L-tyrosyl-gamma-benzyl-D-glutamyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-propyl-L-leucyl-L-valyl-O-benzyl-L-threonyl-O-CH₂-resin is prepared by the method of Example 1, using the corresponding t-Boc-D-glutamic acid derivative instead of t-Boc-D-alanine.

EXAMPLE 22

D-Glu²-α-endorphin is prepared by the method of Example 2 from the peptide resin of Example 21.

EXAMPLE 23

0-2-Bromobenzyloxycarbonyl-L-tyrosyl-D-glutaminyl-glycyl-L-phenylalanyl-L-methionyl-O-benzyl-L-threonyl-O-benzyl-L-seryl-gamma-benzyl-L-glutamyl-N-epsilon-2-chlorobenzyloxy-carbonyl-L-lysyl-O-benzyl-L-seryl-L-glutaminyl-O-benzyl-L-threonyl-L-prolyl-L-leucyl-L-valyl-O-benzyl-L-threonyl-O-CH₂-resin is prepared by the method of Example 1, using the corresponding t-Boc-D-glutamine instread of t-Boc-D-alanine.

EXAMPLE 24

D-Gln$^2$-α-endorphin is prepared by the method of Example 2 from the peptide resin of Example 23.

EXAMPLE 25

0-2-Bromobenzyloxycarbonyl-L-tyrosyl-beta-benzyl-D-aspartyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH$_2$-resin is prepared by the method of Example 1, using the corresponding t-Boc-D-aspartic acid derivative instead of t-Boc-D-alanine.

EXAMPLE 26

D-Asp$^2$-α-endorphin is prepared by the method of Example 2 from the peptide resin of Example 25.

EXAMPLE 27

0-2-Bromobenzyloxycarbonyl-L-tyrosyl-D-asparaginyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH$_2$-resin is prepared by the method of Example 1, using the corresponding t-Boc-D-asparagine instread of t-Boc-D-alanine.

EXAMPLE 28

D-Asn$^2$-α-endorphin is prepared by the method of Example 2 from the peptide resin of Example 25.

EXAMPLE 29

0-2-Bromobenzyloxycarbonyl-L-tyrosyl-N-epsilon-2--chlorobenzyloxycarbonyl-D-lysyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L glutaminyl-O-benzyl-L-threonyl-L-prolyl-L-leucyl-L-valyl-O-benzyl-L-threonyl-O-CH$_2$-resin is prepared by the method of Example 1, using the corresponding t-Boc-D-lysine derivative instead of the t-Boc-D-alanine-resin.

EXAMPLE 30

D-Lys$^2$-α-endorphin is prepared by the method of Example 2 from the peptide resin of Example 29.

EXAMPLE 31

0-2-Bromobenzyloxycarbonyl-L-tyrosyl-N$^G$-tosyl-D-arginyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-O-CH$_2$-resin is prepared by the method of Example 1, using the corresponding t-Boc-D-arginine derivative instead of the t-Boc-D-alanine-resin.

EXAMPLE 32

D-Arg$^2$-α-endorphin is prepared by the method of Example 2 from the peptide resin of Example 31.

EXAMPLE 33

Preparation of 0-2-Bromobenzyloxycarbonyl-L-tyrosyl-D-alanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin.

Using the conditions described in Example 1, the t-Boc-derivatives of each amino acid are successively coupled to a benzhydrylamine resin (0.63g, 0.5 mmole), which is purchased from Beckman Instruments, Palo Alto, Calif.

EXAMPLE 34

D-Ala$^2$-α-endorphin is prepared by the method of Example 2 from the peptide resin of Example 33.

EXAMPLE 35

0-2-Bromobenzyloxycarbonyl-L-tyrosyl-D-leucyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-D-leucine instead of t-Boc-D-alanine.

EXAMPLE 36

D-Leu$^2$-α-endorphin amide is prepared by the method of Example 2 from the peptide resin of Example 35.

EXAMPLE 37

0-2-Bromobenzyloxycarbonyl-L-tyrosyl-D-isoleucylglycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-D-isoleucine, instead of t-Boc-D-alanine.

EXAMPLE 38

D-Ile$^2$-α-endorphin amide is prepared by the method of Example 2 from the peptide resin of Example 37.

Example 39

0-2-Bromobenzyloxycarbonyl-L-tyrosyl-D-valyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine is prepared by the method of example 1, using t-Boc-D-valine, instead of t-Boc-D-alanine.

EXAMPLE 40

D-Val$^2$-α-endorphin amide is prepared by the method of Example 2 from the peptide resin of Example 39.

EXAMPLE 41

0-2-Bromobenzyloxycarbonyl-L-tyrosyl-D-phenylalanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L- lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Box-D-phenylalanine, instead of t-Boc-D-alanine.

EXAMPLE 42

D-Phe$^2$-α-endorphin amide is prepared by the method of Example 2 from the peptide of Example 41.

EXAMPLE 43

0-2-Bromobenzyloxycarbonyl-L-tyrosyl-O-2-bromobenzyloxycarbonyl-D-tyrosyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33 using the t-Boc-D-tyrosine derivative instead of t-Boc-D-alanine.

EXAMPLE 44

D-Tyr$^2$-α-endorphin amide is prepared by the method of Example 2 from the peptide resin of Example 43.

EXAMPLE 45

0-2-Bromobenzyloxycarbonyl-L-tyrosyl-D-tryptophanyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-D-tryptophan, instead of t-Boc-D-alanine.

EXAMPLE 46

D-Tyr$^2$-α-endorphin amide is prepared by the method of Example 2 from the peptide resin of Example 45.

EXAMPLE 47

0-2-Bromobenzyloxycarbonyl-L-tyrosyl-O-benzyl-D-seryl-glycyl-L-phenylalanyl-L-methionyl-O-benzyl-L-threonyl-0-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using the t-Boc-D-serine derivative instead of t-Boc-D-alanine.

EXAMPLE 48

D-Ser$^2$-α-endorphin amide is prepared by the method of Example 2 from the peptide resin of Example 47.

EXAMPLE 49

0-2-Bromobenzyloxycarbonyl-L-tyrosyl-O-benzyl-D-threonyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using the the t-Boc-D-threonine derivative instead of t-Boc-D-alanine.

EXAMPLE 50

D-Thr$^2$α-endorphin amide is prepared by the method of Example 2 from the peptide resin of Example 49.

EXAMPLE 51

0-2-Bromobenzyloxycarbonyl-L-tyrosyl-D-methionylglycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-methionine instead of t-Boc-D-alanine.

EXAMPLE 52

D-Met$^2$-α-endorphin amide is prepared by the method of Example 2 from the peptide resin of Example 51.

EXAMPLE 53

0-2-Bromobenzyloxycarbonyl-L-tyrosyl-gamma-benzyl-D-glutamyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using the t-Boc-glutamic acid derivative instead of t-Boc-D-alanine.

EXAMPLE 54

D-Glu$^2$-α-endorphin amide is prepared by the method of Example 2 from the peptide resin of Example 53.

EXAMPLE 55

0-2-Bromobenzyloxycarbonyl-L-tyrosyl-D-glutaminyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-D-glutamine instead of t-Boc-D-alanine.

EXAMPLE 56

D-Gln$^2$-α-endorphin amide is prepared by the method of Example 2 from the peptide resin of Example 55.

EXAMPLE 57

0-2-Bromobenzyloxycarbonyl-L-tyrosyl-beta-benzyl-D-aspartyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 1, using the t-Boc-aspartic acid derivative instead of t-Boc-D-alanine.

EXAMPLE 58

D-Asp$^2$-α-endorphin amide is prepared by the method of Example 2 from the peptide resin of Example 57.

EXAMPLE 59

0-2-Bromobenzyloxycarbonyl-L-tyryl-D-asparaginyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using t-Boc-asparagine instead of t-Boc-D-alanine.

EXAMPLE 60

D-Asn$^2$-α-endorphin is prepared by the method of Example 2 from the peptide resin of Example 59.

EXAMPLE 61

0-2-Bromobenzyloxycarbonyl-L-tyrosyl-N-epsilon-2-chlorobenzyloxycarbonyl-D-lysyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzhydrylamine resin is prepared by the method of Example 33, using the t-Boc-D-lysine derivative instead of t-Boc-D-alanine.

EXAMPLE 62

D-Lys$^2$-α-endorphin amide is prepared by the method of Example 2 from the peptide resin of Example 61.

EXAMPLE 63

0-2-Bromobenzyloxycarbonyl-L-tyrosyl-N$^G$-tosyl-D-arginyl-glycyl-L-phenylalanyl-L-methionyl-O-benzyl-L-threonyl-O-benzyl-L-seryl-gamma-benzyl-L-glutamyl-N-epsilon-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-benzyhdrylamine resin is prepared by the method of Example 33, using the corresponding t-Boc-D-arginine derivative instead of t-Boc-D-alanine.

EXAMPLE 64

D-Arg$^2$-α-endorphin amide is prepared by the method of Example 2 from the peptide resin of Example 63.

Examples 65–73 illustrate the preparation of the esters of this invention. It will be readily apparent to one skilled in the art that esters of a D-amino acid$^2$ substituted endorphin are prepared by reacting the peptide resins of Examples 1, 3, 5, 7, 9, 11, 13, 15, 17, 19, 21, 23, 25, 27, 29, 31, 33 and 35 with the appropriate alcohol in the presence of base and then proceeding as in Example 2 with hydrogen fluoride treatment and subsequent purification of the desired material.

EXAMPLE 65

The methyl ester of D-Ala$^2$-α-endorphin is prepared from the resin of Example 1 by cleaving the peptide from the resin with methanol (50 ml) in the presence of triethylamine (40 mmoles) at room temperature. Removal of the protecting groups is carried out according to the method of Example 2 by treating the peptide with hydrogen fluoride.

EXAMPLE 66

The ethyl ester of D-Leu$^2$-α-endorphin is prepared by the method of Example 65 from the resin of Example 3, using ethanol in place of methanol and conducting the reaction at elevated temperatures.

EXAMPLE 67

The n-propyl ester of D-Ile$^2$-α-endorphin is prepared by the method of Example 66 from the resin of Example 5, using n-propanol instead of ethanol.

EXAMPLE 68

The isopropyl ester of D-Val$^2$-α-endorphin is prepared from the resin of Example 7, by the method of Example 66, using iso-propanol in place of ethanol.

EXAMPLE 69

The n-butyl ester of D-Phe$^2$-α-endorphin is prepared from the resin of Example 9, by the method of Example 66, using the n-butanol instead of ethanol.

EXAMPLE 70

The tert-butyl ester of D-Tyr$^2$-α-endorphin is prepared from the resin of Example 11 by the method of Example 66, using tert-butanol instead of ethanol.

EXAMPLE 71

The sec-butyl ester of D-Trp$^2$-α-endorphin is prepared from the resin of Example 13 by the method of Example 66, using sec-butanol instead of ethanol.

EXAMPLE 72

The n-pentyl ester of D-Ser$^2$-α-endorphin is prepared from the resin of Example 15 by the method of Example 66, using n-pentanol instead of ethanol.

EXAMPLE 73

The n-hexyl ester of D-Thr$^2$-α-endorphin is prepared from the resin of Example 17 by the method of Example 66, using n-hexanol instead of ethanol.

The following examples are illustrative of the preparation of the alkylamides and dialkylamides of this invention.

EXAMPLE 74

D-Ala$^2$-α-endorphin methylamide is prepared by reacting the peptide resin of Example 1 with a large excess of methylamine in dimethylformamide and removal of the side-chain protecting groups of the cleaved methylamide peptide by treatment with hydrogen flouride in the presence of anisole under the conditions described.

EXAMPLE 75

D-Leu$^2$-α-endorphin, ethylamide is prepared from the peptide-resin of Example 3 by the method of Example 74, using ethylamine in place of methylamine.

EXAMPLE 76

D-Ile$^2$-α-endorphin n-propylamide is prepared from the peptide-resin of Example 5 by the method of Example 74, using n-propylamine in place of methylamine.

The present invention includes within its scope pharmaceutical compositions comprising, as an active ingredient, at least one of the compounds of formula I in association with a pharmaceutical carrier or diluent. The compounds of this invention can be administered by oral, parenteral (intramuscular, intravenous or subcutaneous injection), nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such as compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.001 to 100 mg/kg. of body weight daily are administered to mammals to obtain effective relief from pain or to relieve depression.

The following examples further illustrate the pharmaceutical compositions which are a feature of this invention.

EXAMPLE 77

Tablets weighing 200 mg. and having the following compositions are formulated:

| Ingredient | Mg |
|---|---|
| D-Ala$^2$-β-lipotropin fragment 61–82 | 50 |
| Starch | 120 |
| Collodial silica | 27 |
| Magnesium stearate | 3 |

EXAMPLE 78

Sterile 10 ml. ampules can be prepared containing 10 mg per ml of [D-Ala$^2$]-α-endorphin, ethyl ester 0.1 percent sodium bisulfate, 0.7 percent sodium chloride, and 0.5 percent chlorobutanol as a preservative.

EXAMPLE 79

Topical aqueous formulations for administration by nose drops or nasal spray are formulated containing 1 mg of D-Ile$^2$-α-endorphin amide, 3.8 mgm glycerine, 40 mg. sorbital, 0.02 mg. benzalkonium chloride and purified water g.s. 1 m.

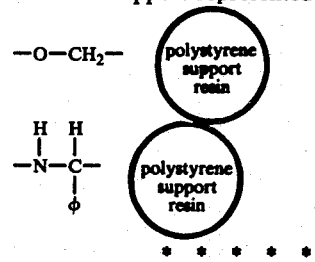

We claim:

1. A hexadecapeptide represented by the formula

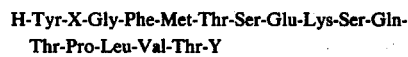

wherein X is a chiral residue of a D-amino acid selected from the group consisting of D-alanine, D-leucine, D-isoleucine, D-valine, D-phenylalanine, D-tryosine, D-tryptophan, D-Serine, D-threonine, D-methionine, D-glutamic acid, D-glutamine, D-aspartic acid, D-asparagine, D-lysine, D-proline, D-histidine and D-arginine; Y is selected from the group consisting of hydroxy, amino, loweralkylamino, diloweralkylamino and loweralkoxy; and the pharmaceutically acceptable salts thereof.

2. A hexadecapeptide of claim 1 wherein Y is hydroxy.

3. A hexadecapeptide of claim 1 wherein Y is amino.

4. A hexadecapeptide of claim 1 wherein Y is loweralkylamino.

5. A hexadecapeptide of claim 1 wherein Y is lower dialkylamino.

6. A hexadecapeptide of claim 1 wherein Y is lower alkoxy.

7. A hexadecapeptide represented by the formula

wherein Y is selected from the group conisting of hydroxy, amino, loweralkylamino, lower dialkylamino, or lower alkoxyl or a pharmaceutically acceptable salt thereof.

8. A hexadecapeptide of claim 6 wherein Y is loweralkylamino.

9. A hexadecapeptide of claim 6 wherein Y is lower dialkylamino.

10. A hexadecapeptide of claim 6 wherein Y is lower alkoxy.

11. D-Ala$^2$-α-endorphin and the pharmaceutically acceptble salt thereof.

12. D-Ala$^2$-α-endorphin amide and the pharmaceutically acceptable salt thereof.

13. A pharmaceutical composition suitable for oral, parenteral, nasal, rectal, vaginal or sublingual administration comprising a therapeutically effective amount of a compound of claim 1 and a pharmaceutically acceptable carrier or diluent.

14. A pharmaceutical composition in accordance with claim 13 suitable for oral administration.

15. A pharmaceutical composition in accordance with claim 13 adapted for parenteral administration.

16. A pharmaceutical composition in accordance with claim 13 adapted for nasal administration.

17. A pharmaceutical composition in accordance with claim 13 adapted for rectal administration.

18. A pharmaceutical composition in accordance with claim 13 adapted for vaginal administration.

19. A pharmaceutical composition in accordance with claim 13 adapted for sublingual administration.

20. Novel hexadecapeptides of the formula

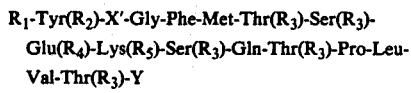
$R_1$-Tyr($R_2$)-X'-Gly-Phe-Met-Thr($R_3$)-Ser($R_3$)-Glu($R_4$)-Lys($R_5$)-Ser($R_3$)-Gln-Thr($R_3$)-Pro-Leu-Val-Thr($R_3$)-Y wherein
X' is a chiral residue of a D-amino acid selected from the group consisting of D-alanine, D-leucine, D-isoleucine, D-valine, D-phenylalanine, D-tyrosine, D-tryptophan, D-serine, D-histidine, D-proline, D-threonine, D-methionine, D-glutamic acid, D-glutamine, D-aspartic acid, D-asparagine, D-lysine and D-arginine with the limitation that when X' is D-tyrosine, D-threonine, D-serine, D-glutamine, D-lysine, D-aspartic acid or D-arginine, X' is a chiral amino acid residue protected by an $R_2$, $R_3$, $R_4$, $R_5$, $R_6$ protecting group;

$R_1$ is a N-terminus solid phase peptide synthesis protecting group selected from the group consisting of acyl-type protecting groups, aromatic urethan-type protecting groups, alkyl-type protecting groups, trialkylsilane groups, or aliphatic urethan protecting groups;

$R_2$ is a protecting group for the phenolic hydroxyl group of tyrosine selected from the group consisting of tetrahydropyranyl, tert-butyl, trityl, benzyl, 2,4-dichlorobenzyl, benzyloxycarbonyl or 2-bromobenzyloxycarbonyl;

$R_3$ is a protecting group for the alcohol hydroxy functions of serine and threonine;

$R_4$ is a protecting group for the gamma carboxyl group of glutamic acid;

$R_5$ is a protecting group for the epsilon amino group of lysine selected from the group consisting of trifluoracetyl, benzyloxycarbonyl, and 2-chlorobenzyloxycarbonyl; and $R_6$ is a protecting group for the guanidine group of arginine;

Y is selected from the group consisting of hydroxy, amino, loweralkylamino, diloweralkylamino, or lower alkoxy and a derivatized insoluble polystyrene resin support represented by the formulae